United States Patent
Agrawal

(10) Patent No.: US 8,302,773 B1
(45) Date of Patent: Nov. 6, 2012

(54) MULTI-COMPARTMENT PACKAGE ASSEMBLY FOR MEDICAL IMPLEMENTS

(75) Inventor: Sony Agrawal, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/093,347

(22) Filed: Apr. 25, 2011

(51) Int. Cl.
*A61B 19/02* (2006.01)
*B65D 73/00* (2006.01)
*B65D 30/22* (2006.01)

(52) U.S. Cl. ......... 206/439; 206/370; 206/484; 383/38
(58) Field of Classification Search ............. 53/425, 53/434, 467, 473; 383/38; 206/370, 438, 206/570–572, 439, 484–484.2
See application file for complete search history.

(56) References Cited

U.S. PATENT DOCUMENTS

| | | | |
|---|---|---|---|
| 2,245,738 A | | 6/1941 | Taylor |
| 3,255,923 A | * | 6/1966 | Soto ........................ 206/484 |
| 3,749,237 A | | 7/1973 | Dorton |
| 3,809,224 A | | 5/1974 | Greenwood |
| 3,861,521 A | | 1/1975 | Burtz |
| 3,939,971 A | | 2/1976 | Tulis |
| 4,496,046 A | * | 1/1985 | Stone et al. ................ 383/38 |
| 4,519,499 A | * | 5/1985 | Stone et al. ................ 383/38 |
| 4,714,595 A | * | 12/1987 | Anthony et al. ............. 206/439 |
| 4,951,815 A | * | 8/1990 | Ulbrich ..................... 206/439 |
| 5,022,521 A | | 6/1991 | Kane |
| 7,040,485 B2 | * | 5/2006 | Gupta et al. ............... 206/484.1 |
| 7,631,760 B2 | * | 12/2009 | Guelzow et al. ............. 206/438 |
| 2010/0256590 A1 | | 10/2010 | Babrowicz et al. |

FOREIGN PATENT DOCUMENTS

GB 2081215 A 2/1982

* cited by examiner

*Primary Examiner* — Bryon Gehman
(74) *Attorney, Agent, or Firm* — Brinks Hofer Gilson & Lione

(57) ABSTRACT

A package is provided to include first and second sheets being releasably sealed together in a manner to define multiple compartments, each having one or more medical implements. A perimeter sealed region can have a seal width greater than an intermediate sealed region. A longitudinal intermediate sealed region and a transverse intermediate sealed region can be arranged within the perimeter sealed region. Formation of the perimeter sealed region along first and second ends of the package can be subsequent to the perimeter sealed region along third and fourth ends of the package. Before the formation, compartments having an opening facing the first end can receive medical implements, and compartments having an opening facing the second end can receive medical implements. The medical implements can remain uncovered by individual pouches when inserted into the respective compartments, thereby reducing manufacturing costs and environmental wastes.

16 Claims, 5 Drawing Sheets

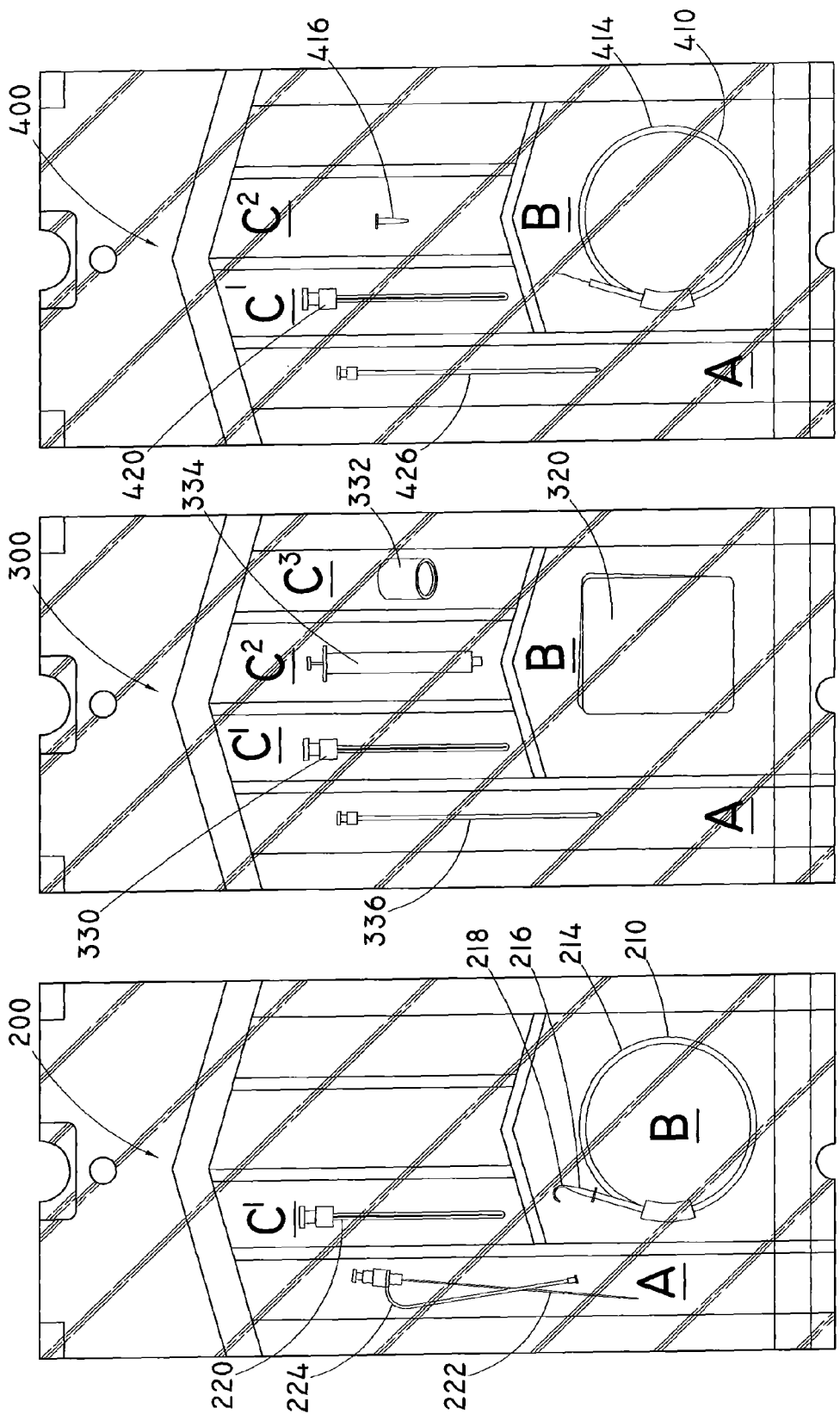

MULTI-COMPARTMENT PACKAGE ASSEMBLY FOR MEDICAL IMPLEMENTS

TECHNICAL FIELD

The present disclosure relates to a package for medical implements, and more particularly, to a multi-compartment package assembly for receiving medical implements.

BACKGROUND

Medical device companies provide assemblies and kits containing medical implements such as needles, syringes, sutures, wire guides, introducer sheath assemblies, and the like to clinicians to be used for particular medical procedures. Commonly, at least some of the medical implements are obtained from external suppliers, which are then combined with the others to form the assemblies and the kits prepared for an end user typically for an intended medical procedure. All of the implements regardless of their source are sterilized, for example by an ethylene oxide (ETO) process, during the assembling process and/or during prior to use by the end user.

Each medical implement is placed either in a single sealed pouch that is combined with other single sealed pouches within a larger sealed outer pouch, or directly within an outer tray with a sealed lid. However, for low volume packaging, outer tray packaging can be relatively expensive per unit cost. Because of the high relative costs, outer pouch sealing can become more commercially viable option.

For outer pouch packages, the assembler typically seals each medical implement within its own single pouch, and then seals a specific combination of medical implements within the outer pouch. To seal within a single pouch, an assembler will insert each medical implement within an individual pouch in a first step. The individual pouches, which are typically purchased from a supplier, are shaped and sized to receive the medical implement therein. The individual pouches are pre-sealed from the supplier along three sides and have an opening at a fourth side to receive the medical implement. After insertion of the medical implement, a seal is formed along the fourth side of each individual pouch by an assembler in a second step. The first and second steps of the assembling process require additional time and labor during the assembling process, and thus results in additional manufacturing costs per assembly or kit.

To seal the single sealed pouches within a larger outer pouch, an assembler will insert all of the individually sealed pouches within a larger outer barrier pouch in a third step. The outer barrier pouch, which is typically purchased from a supplier, has a single compartment that is sized to contain all of the individually sealed pouches which contain the medical implements. The outer barrier pouch is pre-sealed from the supplier along three sides and have an opening at a fourth side to receive all of the individually sealed pouches. A seal is then formed along the fourth side of the outer barrier pouch by an assembler in a fourth step.

To access the medical implements contained within the assembly or kit prior to a medical procedure, the end user would first have to open the outer pouch. The end user would then have to open each of the individual pouches that contain the medical implements. Consequently, each individual pouch is a single use item and discarded as waste. Hence, what is needed is an assembly or a kit for containing medical implements that can be packaged less expensively than the prior art. In particular, multiple medical implements can be assembled within the assembly or the kit in fewer process steps and/or with less material so that the assembly or the kit is environmentally friendly and results in reduced environmental wastes and costs of recycling for end users.

BRIEF SUMMARY

In one embodiment, a multiple compartment package for medical implements or kit is provided herein. The package can include a polymeric first sheet and a gas permeable bacteria resistant second sheet overlaying the first sheet. The first and second sheets can be releasably sealed together to define a perimeter sealed region formed along first, second, third, and fourth ends of the package. Further, the first and second sheets can be releasably sealed together to define intermediate sealed regions formed in an intermediate region of the package defined between the first, second, third, and fourth ends of the package. The perimeter sealed region can have a first width greater than a second width of each intermediate sealed region. The intermediate sealed regions can include at least one longitudinal intermediate sealed region, which extends in a longitudinal direction at least partially between the first and second ends. Further, the intermediate sealed regions can include at least one transverse intermediate sealed region, which extends in a transverse direction at least partially between the third and fourth ends. The intermediate sealed regions can be arranged relative to the perimeter sealed region to define a plurality of compartments. At least one of the compartments has an opening facing the first end of the package to receive at least one first medical implement therein, and at least one of the compartments has an opening facing the second end of the package to receive at least one second medical implement therein prior to formation of the perimeter sealed regions corresponding to the first and second ends of the package.

In another embodiment, one example of the package can be made by a process including one or more of the following steps. At least one first medical implement can be inserted into at least one first compartment that has an opening facing either of the first or second ends of the intermediate product. A third sealed region of the perimeter sealed region can be formed to intersect the first and second sealed regions to close the opening of the at least one first compartment. At least one second medical implement can be inserted into at least one second compartment that has an opening facing the other of the first or second ends of the intermediate product. A fourth sealed region of the perimeter sealed region can be formed to intersect the first and second sealed regions to close the opening of the at least one second compartment, whereby a final product of the package is formed.

In another embodiment, a method of packaging medical implements is provided. The method can include one or more of the following steps. An intermediate product of a multiple compartment package can be formed initially. A polymeric first sheet and a gas permeable bacteria resistant second sheet overlaying the first sheet are provided to define first and second ends of a unit, and third and fourth ends of the unit interconnecting the first and second ends. The first and second sheets can be releasably sealed together to define first and second portions of a perimeter sealed region formed along portions of the third and fourth ends of the unit. The first and second sheets can be releasably sealed together to define intermediate sealed regions formed in an intermediate region of the sheets. The first and second sealed regions of the perimeter sealed region can have a first width greater than a second width of each intermediate sealed region. The intermediate sealed regions can have at least one longitudinal intermediate sealed region, which extends in a longitudinal direction along the third and fourth ends, and at least one transverse intermediate sealed region, which extends in a transverse direction along the first and second ends. The intermediate sealed regions can be arranged relative to the perimeter sealed region to define a plurality of compartments having compartment openings that face at least one of the first end and the second end of the unit, whereby an intermediate product of a package is formed.

BRIEF DESCRIPTION OF THE DRAWINGS

FIGS. 7A-7C illustrate exemplary kit package assemblies.

DETAILED DESCRIPTION OF THE DRAWINGS AND THE PRESENTLY PREFERRED EMBODIMENTS

Figures 1, 2:
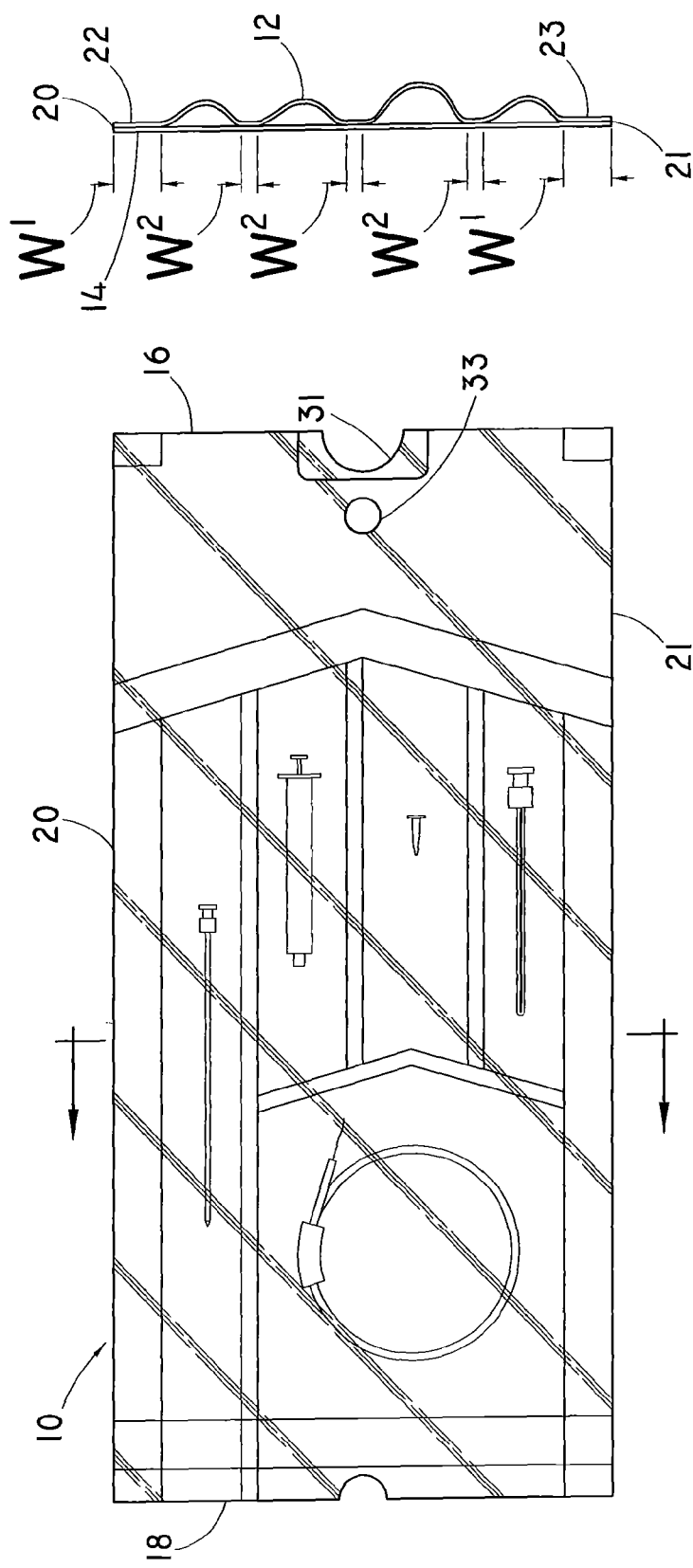
FIG. 1 is a top view of a multiple compartment package for medical implements.
FIG. 2 is a transverse sectional view of the package taken along the lines in FIG. 1.

For the purposes of promoting an understanding of the principles of the present disclosure, reference will now be made to the embodiments illustrated in the drawings, and specific language will be used to describe the same.

FIG. 1 depicts an exemplary package assembly 10 having a plurality of compartments for containing medical implements. Non limiting examples of such medical implements include needles, syringes, sutures, wire guides, introducer sheath assemblies, and the like. A particular combination of medical implements can be pre-selected in order to provide a kit suitable for a particular medical procedure.

In FIGS. 1-2, the package assembly 10 includes a first sheet 12 overlying a second sheet 14. Although the sheets 12, 14 are shown to be rectangular, it is appreciated that the sheets can be provided in a variety of geometric shapes. The first sheet 12 and the second sheet 14 can be sealed together in a manner to define a plurality of compartments, the arrangement shown being merely one non-limiting example of a suitable arrangement of the compartments. The sealing can be performed by bonding, fusing, adhesives, and/or heat sealing techniques. The sheets 12, 14 are arranged to define a first end 16 and a second end 18, generally the top and bottom ends respectively, of the package assembly 10, and a third end 20 and a fourth end 21, generally a pair of sides respectively, of the package assembly interconnecting the first and second ends 16, 18. The third and fourth ends can define longitudinal edges of the package assembly, and the first and second ends can define transverse edges of the package assembly.

The first sheet and the second sheet can be made of a variety of polymer and/or fabric materials. For example, the first sheet 12 can be a polymer film such as polyethylene, polyester, polyester (PET) modified low-density polyethylene (LDPE) laminated film, or a laminate (e.g., metalized PET). In one example, the first sheet is dual laminate material with 0.002-inch LDPE and 0.0005-inch polyester. The first sheet 12 is generally impervious to gas, and may also constitute an impassible barrier to moisture, bacteria, viruses, and other substances that may compromise the sterility or are otherwise detrimental to the implements and the packaging. In one example, the first sheet and the second sheet selected are capable of being sealed together in a manner to maintain sterility.

The second sheet 14 can be made of a material configured to facilitate sterilization procedures. In one instance, the first sheet 14 can be a breathable material that is permeable to permit sterilizing gases such as steam, ethylene oxide, or Freon, and/or transparent to permit e-beams and gamma rays used in irradiative sterilization. The second sheet 14 may also constitute an impassible barrier to moisture, bacteria, viruses, and other substances that may compromise the sterility or are otherwise detrimental to the implements and the packaging. One example of a material for the second sheet 14 having one or more of the properties is sold under the trademark TYVEK® (2FS, 1059B and 1073B), which is available from Medical Packaging Division of E.I DuPont de Nemours and Company. TYVEK® is a lightly consolidated or unconsolidated fabric made from spun high-density polyethylene (HDPE), which is also strong, puncture-resistant and tear-resistant.

Figure 3:
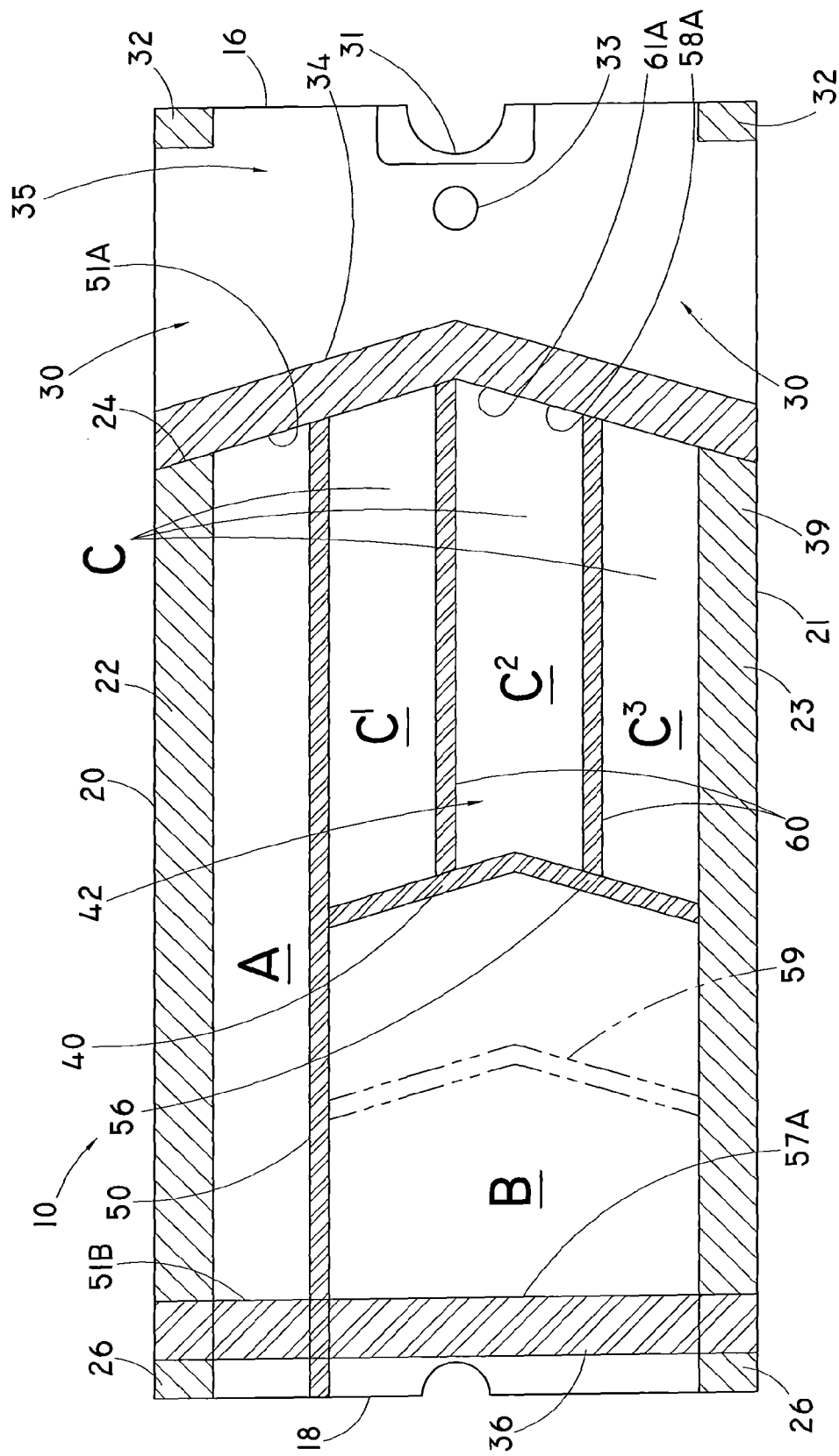
FIG. 3 is a top view of a second sheet of a multiple compartment package with a first sheet removed.

In FIG. 3, first and second sealed regions 22, 23 can be formed at least partially along the respective third and fourth ends 20, 21 of the package assembly 10. The first and second sealed regions 22, 23 each can have a first end 24 proximate the first end 16 of the package assembly 10 and a second end 26 proximate the second end 18 of the package assembly 10. The second end 26 of the first and second sealed regions 22, 23 can be contiguous with the second end 18 of the package assembly 10. The first end 24 of the first and second sealed regions 22, 23 may be located at least halfway along the sides 20 to terminate at some point that is closer to the first end 16 than the second end 18 of the package assembly 10. A portion 30 of the sheets 12, 14 along the third and fourth ends 20, 21 may not be sealed together. The corners 32 where the third and fourth ends 20, 21 interconnect to the first end 16 may be sealed such as by a tack seal.

A third sealed region 34 can be formed along the first end 16 of the package assembly 10. The third sealed region 34 can intersect portions of the first and second sealed regions 22, 23, which may be close in proximity to the first ends 24 of the first and second sealed regions. The third sealed region 34 may be contiguous with the first end 16 of the package assembly 10. Preferably, the third sealed region 34 can be spaced from the first end 16 as shown in the figures to define a region 35 where the first and second sheets remain unsealed. The third sealed region 34 can be linear or can be configured into other shapes to facilitate peelability of the first and second sheets along the sealed region, such as a V-shape or shaped like a chevron. A thumb notch 31 can be provided along the first end 16, preferably centrally located. The thumb notch 31 can be circular or rectangular. A hang hole 33 can also be provided along the first end 16, preferably centrally located just below the thumb notch 31.

A fourth sealed region 36 can be formed along the second end 18 of the package assembly 10. The fourth sealed region 36 can intersect portions of the first and second sealed regions 22, 23, which may be close in proximity to the second ends 26 of the first and second sealed regions. The fourth sealed region 36 may be contiguous with the second end 18 of the package assembly 10 or may be spaced from the second end 18 as shown in the figures. The first, second, third and fourth sealed regions can be portions that define a perimeter sealed region 39 of the package assembly 10. In FIG. 2, the seal width W1 of the first, second, third and fourth sealed regions can be any size depending on the user needs, the size of the package, size of the medical implement, bulging of the packaging due to the size of the medical implement, and the like.

Bulging in the package can tend to weaken the integrity of the sealed region. Exemplary seal width W1 sizes can include up to about 1-inch, such as, for example, 0.125-inch, 0.25-inch, 0.375-inch, 0.5-inch. Preferably, the seal width W1 is at least about 0.375 inches to sufficiently withstand the problems of bulging.

Referring back to FIG. 3, one or more intermediate sealed regions 40 can be formed at least partially along an intermediate region 42 located between the first and second ends 16, 18 and the third and fourth ends 20, 21 of the package assembly 10. The intermediate sealed regions 40 together with the first and second sealed regions 22, 23 and the third and fourth sealed regions 34, 36 can be arranged to define the plurality of compartments as described below. As shown in FIG. 2, the seal width W2 of the intermediate sealed regions can be any size and may be the same size as the seal width W1. However, preferably, the seal width W2 is less than the seal width W1. The size of the seal width W2 can depend on the user needs, the size of the package, size of the medical implement, bulging of the packaging due to the size of the medical implement, and the like. Exemplary seal width W2 sizes can include up to about 1-inch, such as, for example, 0.125-inch, 0.25-inch, 0.375-inch, 0.5-inch. Preferably, the seal width W2 is at least about 0.125 inches for a suitable seal and to facilitate peelability of the first and second sheets. The seal width W2 can be greater than about 0.125 inches, such as about 0.375-inches, for overcoming the problems of bulging. In other words, as additional sealed regions are provided, it can be more difficult for the end user to peel the first and second sheets. Thus, the narrower seal widths along the intermediate region can be sufficiently effective in isolating each medical implement, while allowing for easier peelability between the sheets.

The compartments can have compartment openings facing at least one of the first and second ends 16, 18 to receive one or more medical implements therein before the third and fourth sealed regions 34, 36 are formed. After the third and fourth sealed regions are formed, it is desirable to open the package assembly from the first end 16 by peeling the first and second sheets 12, 14 away from one another.

In FIG. 3, intermediate sealed region 40 may include a first longitudinal intermediate sealed region 50 that extends generally in a same direction as the third and fourth ends of the package assembly 10. The first longitudinal intermediate sealed region 50 can intersect the first and second sealed regions 34, 36 to form a first compartment A. In one example, the first compartment A is defined between the first longitudinal intermediate sealed region 50 and one of the first and second sealed regions 22, 23, thereby forming a compartment for lengthier medical implements. Before the third and fourth sealed regions 34, 36 are formed, the first compartment A can include both of a first opening 51A facing the first end 16 of the package assembly 10 and a second opening 51B facing the second end 18 of the package assembly.

The intermediate sealed region 40 may include a second transverse intermediate sealed region 56 that extends generally in a same direction as the first and second ends of the package assembly 10. Preferably, the second transverse intermediate sealed region 56 can extend substantially transverse to the first longitudinal intermediate sealed region 50. The second transverse intermediate sealed region 56 can intersect the first longitudinal intermediate sealed region 50 and/or one of the first and second sealed regions 22, 23 to form more than one compartment on either side. For example, a second compartment B can be formed having a compartment opening 57A facing the second end 18 of the package assembly 10 before the third and fourth sealed regions 34, 36 are formed, thereby forming a compartment for wider medical implements. A third compartment C can also be formed having a compartment opening 58A facing the first end 16 of the package assembly before the third and fourth sealed regions 34, 36 are formed. The second transverse intermediate sealed region 56 can be linear or can be configured into other shapes to facilitate peelability of the sheets along the sealed region, such as a V-shape or shaped like a chevron. Additional transverse intermediate sealed regions, such as region 59 shown in dashed lines, can be formed, e.g., to further segment the compartment B into more compartments. This can beneficially provide compartments containing sterile medical implements that can be subsequently opened later in the medical procedure.

The intermediate sealed region 40 may also include a third longitudinal intermediate sealed region 60 that extends generally in a same direction as the third and fourth ends 20, 21. The third longitudinal intermediate sealed region 60 can intersect the second transverse intermediate sealed region 56 and one of the third and fourth sealed regions 34, 36 to further segment the second compartment B or the\third compartment C into additional compartments. Before the third and fourth sealed regions 34, 36 are formed, the further segmented compartments of the first or second compartments B, C can have compartment openings facing only the first end or only the second end of the package, respectively. For example, in FIG. 3, a pair of third longitudinal intermediate sealed regions 60 is formed to further segment the compartment C into three compartments C1, C2, and C3. These compartments can have compartment openings 61A facing only the first end 16 of the package assembly 10 before the third and fourth sealed regions 34, 36 are formed, thereby forming compartments for smaller medical implements. FIGS. 1 and 3 depict one configuration of compartment arrangement.

It can be appreciated by those skilled in the art that other compartment arrangements than what is shown in the figures are possible, including more or fewer longitudinal and/or transverse intermediate regions. It is also contemplated that each sealed region can be linear and substantially in alignment with the ends to define four-sided compartments as shown in the figures, but can also be non-linear, diagonal, or even asymmetric to define other geometrically shaped compartments or irregularly shaped compartments.

With additional reference to FIGS. 4-5, a method of packaging medical implements will now be described. The method can include taking a package configuration that can have portions of the first and second sheets sealed together to define an intermediate product, and then sealing respective portions of the intermediate product to make a final product. The provision of an intermediate product can allow for high volume production of the intermediate product by a supplier to reduce the manufacturing costs of the package assembly, while allowing customization by the assembler with respect to component selection and final sealing. However, it can be appreciated that the package assembly can be made without distinction between an intermediate product and a final product, and thus the steps of releasably sealing the first and second sealed regions and the intermediate sealed regions can be performed similar to the sealing of the third and fourth sealed regions.

Figure 4:
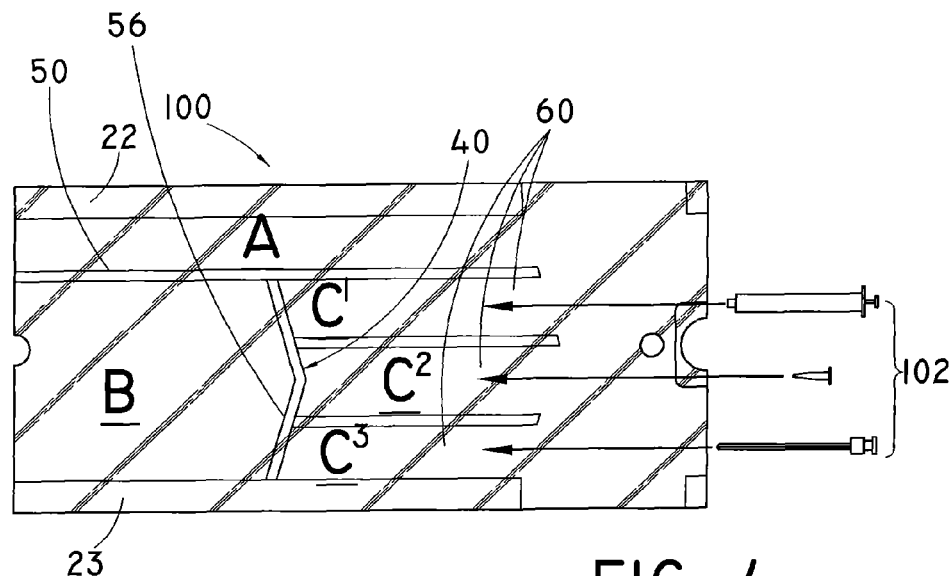
FIGS. 4-5 are top views depicting a method of packaging medical implements.
Figure 5:
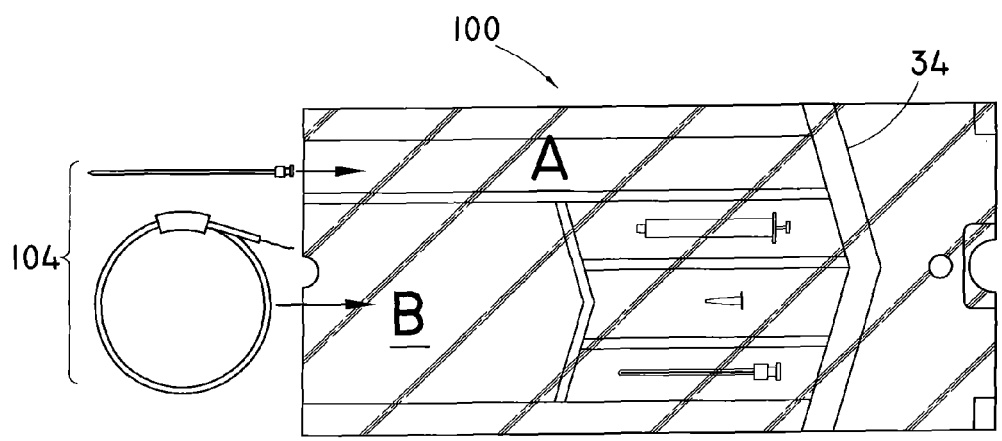

In FIG. 4, the intermediate product 100 can have one or more pre-sealed regions that form one or more of compartments A-C with compartment openings for receiving the medical implements. The compartment openings can face the respective first and second ends. For instance, the intermediate product 100 can include the first sheet 12 and the second sheet 14 having pre-sealed regions such as the first and second side sealed regions 22, 23 and a plurality of intermediate sealed regions 40, such as longitudinal and transverse intermediate sealed regions 50, 56, 60. The pre-sealed regions are arranged to define one or more of the first compartments A, one or more of the second compartments B, one or more the third compartments C, and/or further segments thereof, such as compartments C1-C3. However, the third and fourth sealed regions can be applied in subsequent steps following insertion of the medical implements. This allows external access to the compartments in the intermediate product 100. It can be appreciated by those skilled in the art that the first and second sheets can be pre-sealed to have various configurations of compartments that are illustrated herein, as described above.

One or more first medical implements 102 can be inserted into compartments only having compartment openings that face one of the first end 16 or the second end 18. Typically, one medical implement is inserted within one compartment. FIG. 4 depicts three first medical implements, such as, e.g., a syringe, a wire guide inserter, and an introducer needle contained with a needle holder, being inserted within the respective third compartments C1-C3. The first and second sheets 12, 14 are sealed together to form the third sealed region 34 or the fourth sealed region 36. FIG. 5 depicts the formation of the third sealed region 34. Next, one or more second medical implements 104 can be inserted into the remaining compartments of the intermediate product 100. For example, FIG. 5 shows two second medical implements 104, such as, e.g., an introducer sheath and/or dilator and a wire guide contained within a coiled holder, being inserted into the compartments A, B. The first and second sheets are then sealed together to form the other of the third sealed region 34 or the fourth sealed region 36. In this example, the fourth sealed region 36 will be formed to form a final product such as the package assembly 10 in FIG. 1. When the sealed region 59 is present, the medical implement would be inserted first from the second end 18, and formation of the sealed region 59 can capture the medical implement within the formed compartment between the sealed region 59 and the sealed region 56. Thereafter, another medical implement can be inserted in the remaining portion of the compartment B before formation of the fourth sealed region 36.

The first and second sheets can be sealed to one another with a sealer at a predetermined temperature, time, and pressure that is sufficient to seal the materials of the first sheet and the second sheet together. One such sealer can be found at Sencorp Systems (Hyannis, Mass.). The sealer can include a die that is shaped for the intended shape of the sealed region. It is contemplated that the medical implements can be individually sealed into pouches having similar materials as the first and second sheets before being inserted into the compartments. However, it is preferred that the medical implements be directly inserted within the multiple compartments of the package assembly without pouches. As a result, additional time and labor, as well as materials (i.e., no individual pouches for medical implements), to individually seal each medical implement in its own pouch can be eliminated. This arrangement can result in a single package with multiple medical implements and in a reduction in manufacturing costs per a single package assembly or kit.

The first and second medical implements can remain non-sterile during insertion into the respective compartments. Thereafter, the final product package assembly 10 and the medical implements received therein can be sterilized by various means known in the art. For example, the final package assembly 10 can be exposed to sterilizing gases such as steam, ethylene oxide (ETO), or Freon, and/or radiation such as e-beams and gamma rays used in irradiative sterilization. Since the first and second sheets are configured to prevent the passage of bacteria, the first and second medical implements of the package assembly will remain sterile until the seal formed by the respective sealed regions is broken.

Figure 6:
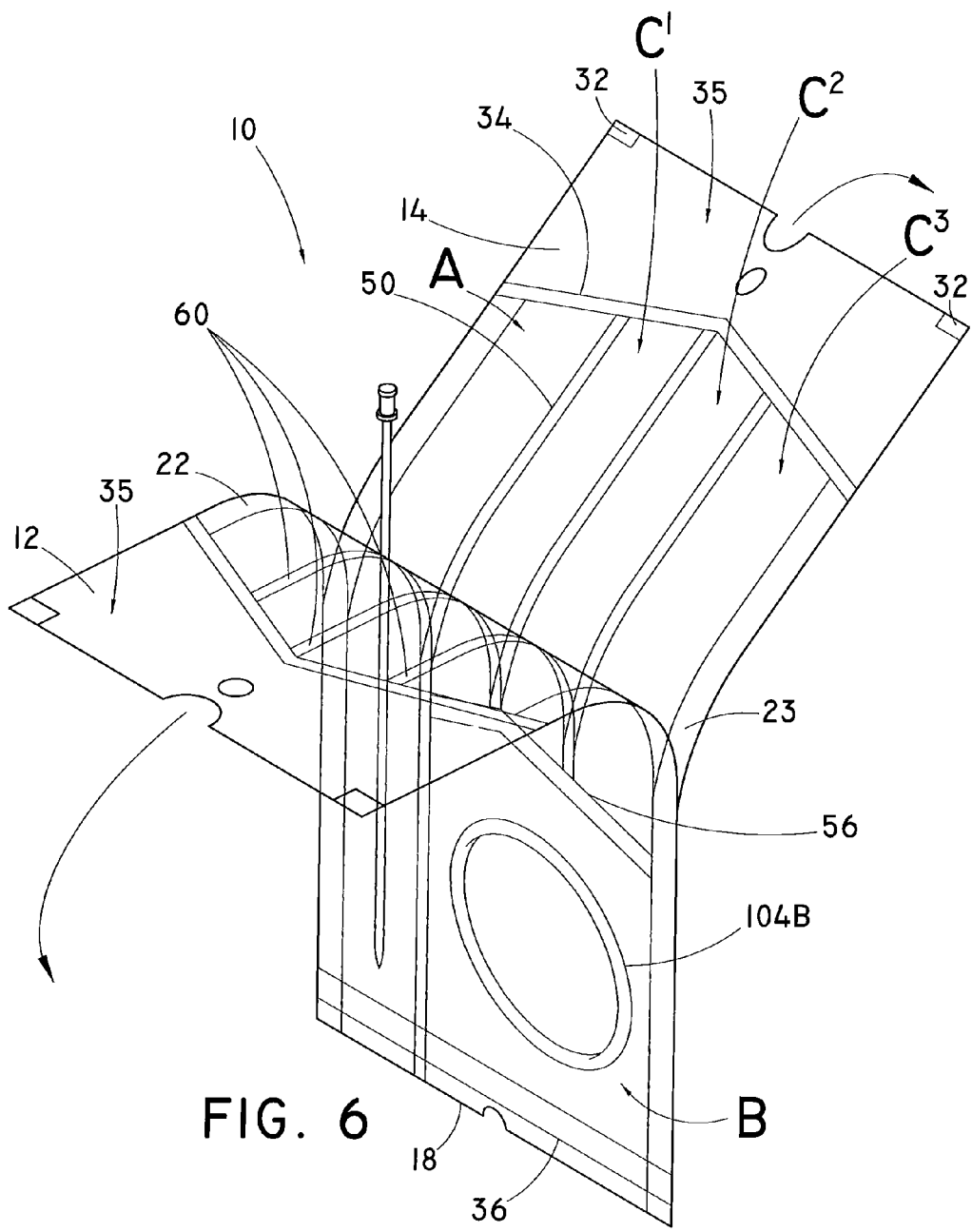
FIG. 6 is a perspective view of an intermediate step of opening the package of FIG. 1.

In FIG. 6, an end user can conveniently open the package assembly 10 by peeling the first and second sheets 12, 14 away from each other. Hands of the end user can grab portions of each sheet at the region 35 where the first and second sheets remain unsealed proximate the first end 16. A force can be applied with hand in opposite directions so that the corner seals 32 when present can be broken first. The force can be redirected to partially outward and toward the second end 18, in a direction represented by the arrows, to peel the first and second sheets 12, 14 apart from one another, thereby breaking the entire third sealed region 34 for external access to the compartments adjacent the third sealed region. As a result, medical implements within these adjacent compartments having compartment openings along the third sealed region, such as compartments A, C1, C2, and C3, can be removed, although the medical implement 104A is shown extending from the compartment A. As the force is continued in the direction of the arrows, the first and second sheets 12, 14 are continued to be peeled apart from one another. Consequently, at least portions of the first and second sealed regions 22, 23, as well as at least portions of the longitudinal intermediate sealed regions 50, 60, are broken. FIG. 6 shows the first and second sheets 12, 14 partially opened with at least the compartment B, which contains a sterile medical implement 104B, still yet to be broken.

This action is continued until the transverse intermediate sealed region 56 is broken for external access to the compartments adjacent such region. As a result, medical implements, such as the medical implement 104B, within these adjacent compartments having compartment openings along the transverse intermediate sealed region, such as compartment B, can be removed. The package assembly 10 can provide a multiple compartment package where external access to medical implements can be gained with only a single peel action. Some medical implements can remain sealed within compartments, while other medical implements are being used during the procedure. When individual pouches for the medical implements are not used, the end user can quickly access the sterilized medical implements without opening additional pouches. Furthermore, the additional wastes created by the individual pouches can be avoided. Hence, the assembly or the kit can be more environmentally friendly with the reduction of environmental wastes and costs of recycling for end users.

It is contemplated that other package or kit arrangements are possible. One kit package assembly 200 is shown in FIG. 7A. The assembly 200 includes a wire guide system 210 can be located in any of the compartments, such as the compartment B. The system 210 can include a wire guide contained within a wire guide holder that is coiled, shown as reference number 214. The system may include a wire guide inserter 216, and the wire guide may include curved distal tip, such as a J-tip 218. An introducer needle contained with a needle holder, shown as reference number 220, can be located in any of the compartments, such as the compartment C1. The introducer needle can have a bore extending therethrough to permit the wire guide to pass through after the needle has gained percutaneous access to a body vessel. An introducer sheath 222, with or without a dilator, can be located in any of the compartments, such as the compartment A. The introducer sheath 222 can have a proximal fitting with a sidearm fitting for the coupling a flexible tube 224. The flexible tube 224 can be used for flushing and/or infusion of a fluid. One example of a package assembly 200 is the Check-Flo Performer® introducer set, which is commercially provided by Cook Medical (Bloomington, Ind.).

FIG. 7B illustrates another kit package assembly 300. The assembly 300 can include a drape or sterile cloth 320 that can be located in any of the compartments, such as the compartment B. An introducer needle contained with a needle holder, shown as reference number 330, can be located in any of the compartments, such as the compartment C1. The introducer needle can have a bore extending therethrough to permit the wire guide to pass through after the needle has gained percutaneous access to a body vessel. A needle holder 332 can be located in any of the compartments, such as the compartment C3, for facilitating the insertion of the introducer needle. A syringe 334 can be located in any of the compartments, such as the compartment C2. A fluid, such as saline, can be introduced within the syringe. The fluid-filled syringe may then be coupled to the introducer needle or an introducer sheath and/or dilator for flushing and/or infusion. An introducer sheath 336, with or without a dilator, can be located in any of the compartments, such as the compartment A.

FIG. 7C illustrates another kit package assembly 400. The assembly 400 includes a wire guide system 410 can be located in any of the compartments, such as the compartment B. The system 410 can include a wire guide contained within a wire guide holder that is coiled, shown as reference number 414. A wire guide inserter 416 that can be coupled to the wire guide can be located with any of the compartments, such as the compartment C2. An introducer needle contained with an needle holder, shown as reference number 420, can be located in any of the compartments, such as the compartment C1. The introducer needle can have a bore extending therethrough to permit the wire guide to pass through after the needle has gained percutaneous access to a body vessel. An introducer sheath 426, with or without a dilator, can be located in any of the compartments, such as the compartment A. One example of a package assembly 400 is the Check-Flo Performer® introducer set—Micropuncture® Access, which is commercially provided by Cook Medical (Bloomington, Ind.). Although specific components are described with specific package assemblies, it can be appreciated by those skilled in the art that the components are only representative of the many types of components that can be sealed within the package. Further, it is contemplated that the components are interchangeable among the illustrated packages.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

What is claimed is:

1. A multiple compartment package for medical implements, comprising:
   a polymeric first sheet; and
   a gas permeable bacteria resistant second sheet overlaying the first sheet to define first and second ends of the package, and third and fourth ends of the package interconnecting the first and second ends;
   the first and second sheets being releasably sealed together to define a perimeter sealed region formed along the first, second, third, and fourth ends of the package, and releasably sealed together to define intermediate sealed regions formed in an intermediate region of the package defined between the first, second, third, and fourth ends of the package, the perimeter sealed region having a first width greater than a second width of each intermediate sealed region, wherein the intermediate sealed regions comprise at least one longitudinal intermediate sealed region which extends in a longitudinal direction at least partially between the first and second ends, and at least one transverse intermediate sealed region which extends in a transverse direction at least partially between the third and fourth ends, wherein the intermediate sealed regions are arranged relative to the perimeter sealed region to define a plurality of compartments,
   wherein at least one of the compartments has an opening facing the first end of the package to receive at least one first medical implement therein, and at least one of the compartments has an opening facing the second end of the package to receive at least one second medical implement therein prior to formation of the perimeter sealed region corresponding to the first and second ends of the package.

2. The package of claim 1, wherein the at least one longitudinal intermediate sealed region comprises one or more first segments that intersect portions of the perimeter sealed region corresponding to the first and second ends of the package to define one or more first compartments with openings facing both of the first and second ends of the package before said formation.

3. The package of claim 2, wherein one of the first segments is adjacent to a portion of the perimeter sealed region along one of the third and fourth ends of the package.

4. The package of claim 2, wherein the at least one transverse intermediate sealed region intersects one of the third and fourth ends and the first segment to define a second compartment with an opening facing the first end of the package before said formation, and to define a third compartment with an opening facing the second end of the package before said formation.

5. The package of claim 1, wherein the at least one longitudinal intermediate sealed region comprises one or more third segments that intersect both of portions of the perimeter sealed region along either the first end or the second end of the package and the at least one transverse intermediate sealed region to define one or more third compartments with an opening facing either of the first end or the second end of the package before said formation.

6. The package of claim 1, wherein a portion of the perimeter sealed region along the first end of the package has a chevron shape.

7. The package of claim 1, wherein the at least one transverse intermediate sealed region has a chevron shape.

8. The package of claim 1, wherein the first polymeric sheet comprises a low-density polyethylene (LDPE) layer and a polyester layer.

9. The package of claim 1, wherein the second sheet comprises a high-density polyethylene spun fabric.

10. The package of claim 1, wherein the at least one transverse intermediate sealed region is disposed such that when the first and second sheets are peeled, one of the compartments formed by the at least one transverse sealed region remains sealed while one of the compartments is opened to provide external access to the at least one first medical implement contained therein.

11. The package of claim 1, wherein the at least one transverse intermediate sealed region comprises a first transverse intermediate sealed region and a second transverse intermediate sealed region.

12. A multiple compartment package for medical implements, wherein the package includes an intermediate product having a polymeric first sheet, and a gas permeable bacteria resistant second sheet overlaying the first sheet to define first and second ends of the intermediate product, and third and fourth ends of the intermediate product interconnecting the first and second ends, the first and second sheets being releasably sealed together to define first and second sealed regions of a perimeter sealed region that are formed along portions of the respective third and fourth ends of the intermediate product, and releasably sealed together to define intermediate sealed regions formed in an intermediate region of the intermediate product, the first and second intermediate sealed regions of the perimeter sealed region having a first width greater than a second width of each intermediate sealed region, wherein the intermediate sealed regions comprise at least one longitudinal intermediate sealed region which extends in a longitudinal direction, and at least one transverse intermediate sealed region which extends in a transverse direction, wherein the intermediate sealed regions are arranged relative to the first and second sealed regions of the perimeter sealed region to define a plurality of compartments having compartment openings that face at least one of the first end and the second end of the intermediate product, the package made by a process comprising:

inserting at least one first medical implement into at least one first compartment that has an opening facing either of the first or second ends of the intermediate product;

forming a third sealed region of the perimeter sealed region that intersects the first and second sealed regions to close the opening of the at least one first compartment;

inserting at least one second medical implement into at least one second compartment that has an opening facing the other of the first or second ends of the intermediate product; and forming a fourth sealed region of the perimeter sealed region that intersects the first and second sealed regions to close the opening of the at least one second compartment, whereby a final product of the package is formed.

13. The package of claim 12, wherein the at least one longitudinal intermediate sealed region comprises one or more first segments that intersect portions of the perimeter sealed region along the first and second ends of the package to define one or more first compartments with openings facing both of the first and second ends of the package prior to the forming steps.

14. The package of claim 13, wherein one of the first segments is adjacent to a portion of the perimeter sealed region along one of the third and fourth ends of the package.

15. The package of claim 13, wherein the at least one transverse intermediate sealed region intersects one of the third and fourth ends and the first segment to define a second compartment with an opening facing the first end of the package before said formation, and to define a third compartment with an opening facing the second end of the package prior to the forming steps.

16. The package of claim 12, wherein the at least one longitudinal intermediate sealed region comprises one or more third segments that intersect both of portions of the perimeter sealed region along either the first end or the second end of the package and the at least one transverse intermediate sealed region to define one or more third compartments with an opening facing either of the first end or the second end of the package prior to the forming steps.

* * * * *

UNITED STATES PATENT AND TRADEMARK OFFICE
CERTIFICATE OF CORRECTION

Page 1 of 1

PATENT NO. : 8,302,773 B1
APPLICATION NO. : 13/093347
DATED : November 6, 2012
INVENTOR(S) : Sony Agrawal It is certified that error appears in the above-identified patent and that said Letters Patent is hereby corrected as shown below:

On the Title Page

Left Column, after Item (22) insert a new item as follows:
--(65)    Prior Publication Data
US/2012/0267272 A1    October 25, 2012--.

Signed and Sealed this
Second Day of July, 2013

Teresa Stanek Rea
*Acting Director of the United States Patent and Trademark Office*